US012383301B2

(12) United States Patent
Baid et al.

(10) Patent No.: US 12,383,301 B2
(45) Date of Patent: Aug. 12, 2025

(54) SAFETY INTRODUCER NEEDLE ASSEMBLY

(71) Applicant: POLY MEDICURE LIMITED, Faridabad (IN)

(72) Inventors: Rishi Baid, New Delhi (IN); Raunak Gupta, Faridabad (IN)

(73) Assignee: POLY MEDICURE LIMITED, Faridabad (IN)

( * ) Notice: Subject to any disclaimer, the term of this patent is extended or adjusted under 35 U.S.C. 154(b) by 1028 days.

(21) Appl. No.: 17/432,789

(22) PCT Filed: Feb. 20, 2020

(86) PCT No.: PCT/IB2020/051412
§ 371 (c)(1),
(2) Date: Aug. 20, 2021

(87) PCT Pub. No.: WO2020/170180
PCT Pub. Date: Aug. 27, 2020

(65) Prior Publication Data
US 2022/0000517 A1  Jan. 6, 2022

(30) Foreign Application Priority Data

Feb. 20, 2019 (IN) .............................. 201911006705

(51) Int. Cl.
*A61B 17/34* (2006.01)
*A61B 17/00* (2006.01)

(52) U.S. Cl.
CPC ...... *A61B 17/3403* (2013.01); *A61B 17/3496* (2013.01); *A61B 2017/00924* (2013.01);
(Continued)

(58) Field of Classification Search
CPC ............ A61B 17/3403; A61B 17/3496; A61B 2017/3413; A61B 2017/3454; A61M 25/0612
See application file for complete search history.

(56) References Cited

U.S. PATENT DOCUMENTS

2009/0177114 A1  7/2009  Chin et al.
2010/0317963 A1  12/2010  Clancy
2016/0375225 A1  12/2016  Baid

FOREIGN PATENT DOCUMENTS

EP   3003450 A1   4/2016
WO   2011154767 A1   12/2011
WO   2015082559 A1   6/2015

OTHER PUBLICATIONS

First Examination Report issued by the Indian Patent Office for Indian Patent Application No. 201911006705, dated Jun. 16, 2021.
International Search Report issued for International Application No. PCT/IB2020/051412, dated May 20, 2020.
(Continued)

*Primary Examiner* — Ashley L Fishback
(74) *Attorney, Agent, or Firm* — Bradley Arant Boult Cummings LLP; Henry B. Ward, III

(57) ABSTRACT

A safety introducer needle assembly having an introducer needle defining an axial direction, the needle having an outer surface and an inner surface defining a lumen which extends along the length of the needle in the axial direction; the outer surface defined by a wall of the needle forming a needle shaft that extend along the axial direction having a distal end and a proximal end, wherein the proximal end connected to a needle hub and the distal end comprising a sharp bevelled tip wherein the needle has a roughened or echogenic region having echogenic features; and a needle tip protector housed in a safety barrel and slidably arranged on the needle shaft from moving beyond the needle tip and wherein the safety barrel is engageably attached to the needle hub.

20 Claims, 9 Drawing Sheets

(52) U.S. Cl.
CPC ................ *A61B 2017/3413* (2013.01); *A61B 2017/3454* (2013.01)

(56) References Cited

OTHER PUBLICATIONS

Written Opinion issued for International Application No. PCT/IB2020/051412, dated May 20, 2020.

SAFETY INTRODUCER NEEDLE ASSEMBLY

The invention generally relates to safety introducer needle assembly, methods of fabrication and methods of its use. In particularly, the invention relates to a needle having echogenic feature for use with an ultrasound imaging system to provide real-time location of the insertion and guidance at the time the device is implanted in a patient and having enhanced safety features.

More particularly, the present invention relates to a safety introducer needle assembly having a safety mechanism for use in medical procedures, and in particular to safety introducer needle assemblies including a needle having echogenic feature and a safety barrel having a needle tip protector to cover a tip of a needle to prevent accidental needlestick injuries.

BACKGROUND OF THE INVENTION

There are a variety of needles available for different medical and surgical uses. For example, intravenous catheters are utilized in various applications for supplying or withdrawing fluids to or from the body. Medical devices having needles for subcutaneous use are also known in the medical field. For example, biopsy needles are used to capture and remove internal tissues while avoiding invasive surgery. When performing medical procedures, often targeted bodily areas are surrounded by blood vessels or internal organs which can cause difficulties with accurate percutaneous positioning of medical devices.

Ultrasonography has been used to obtain images of medical devices inside a patient's body that would otherwise not be possible through direct visualization, the image quality is often less than optimal. This is, in part, because many medical devices do not inherently possess optimal reflective properties with respect to ultrasound waves.

The introduction of ultrasound imaging in the field of medical technology has greatly influenced the field of percutaneous tissue biopsy in the recent times. The use of tissue imaging devices that utilize ultrasound waves allows the physician to "see" inside the body and visually guide the needle to the tumor mass. The inherent problem in visualizing the needle is that the angle of entry of the needle into the body in relationship to the direction of the generation of ultrasound waves precludes an optimized reflection of the ultrasound waves back to the transceiver, thus making it extremely difficult to see the needle in the ultrasound image and locate the needle tip in the image in relationship to the anatomic structures of the body.

Echogenicity or echogeneity is the ability to bounce an echo, e.g. return the signal in ultrasound examinations. In other words, echogenicity is higher when the surface bouncing the sound echo reflects increased sound waves. Needle tip visualization is fundamental to the safety and efficacy of ultrasound-guided injection. However, it can be extremely challenging to visualize the needle tip especially at steep insertion angles without echogenicity.

To increase image clarity, echogenic enhancements which cause an altered or improved reflective response of ultrasound waves can be applied to a medical device and can cause greater ultrasound image clarity of the device. To remedy this, certain medical devices have been designed to possess enhanced sound wave reflectivity, i.e., echogenicity. This in turn can increase accuracy when positioning the medical device. For example, it is known to apply echogenic enhancements near the tip of a needle so that the tip location is known with greater accuracy. It is also known to roughen, by bead-blasting, the outer surface of the needle to improve its echogenicity. A needle for echogenicity is generally known in the art. Echogenicity provide an acoustic impedance different from the surrounding biological tissue or fluid.

There is a constant need for echogenically-enhanced medical devices which can provide an ultrasound image that is more consistent and having better quality across a range of insertion angles and frequencies and body areas. Such echogenically-enhanced medical devices can improve the physician's confidence in placing a medical device.

The procedures for removing a needle from a patient commonly require a medical practitioner to use one hand to place pressure at the wound site or puncture site where the needle is being withdrawn, while removing the needle device with the other hand. It is also common practice for an attending medical practitioner to give higher priority to care for the wound than is given to disposal of a needle. In the case of typical needle devices without safety shields or guards, such priority either requires the convenience of an available sharps container within reach or another means for safe disposal without leaving the patient's side.

An exposed needle tip creates a danger of accidental needle stick injuries which can leave medical personnel vulnerable to the transmission of various blood-borne pathogens, such as HIV and hepatitis etc. Problems of current safety devices include difficulty of use and high cost due to their complexity and number of parts.

Although several alternate needles having echogenicity are available, a need still exists for a needle with safety features against accidental needle stick injuries. While needle tip protectors have been developed to protect the medical personnel from needle stick injuries, improvements on the cost, ease of use, and effectiveness of these needle tip protectors are a constant need. Therefore, it would be beneficial to have a safety mechanism that is easily activated by medical personnel, adequately protects the needle having echogenic feature from accidental needle stick injury, and is economical to manufacture.

SUMMARY AND OBJECTS OF THE INVENTION

A primary object and advantage of the present invention is to provide a safety introducer needle assembly including a needle having echogenic feature and having improved safety features.

It is another object of this invention to provide a safety introducer needle assembly including a safety barrel having a needle tip protector to cover a tip of the needle to prevent accidental needlestick injuries.

It is another object of this invention to provide a safety barrel having a needle tip protector that is simple and easy to use.

It is another object of this invention to provide a needle tip protector that automatically covers the sharp distal tip of the introducer needle upon withdrawal of the introducer needle.

It is another object of the present invention to provide a needle with enhanced echogenicity and having improved safety features.

It is another object of the present invention to provide an improved needle design to more reliably visualize the design of the needle under ultrasound guided biopsy procedures.

It is another object of the present invention to provide a needle design that allows the visualization of the needle at any angle of entry into the body in relationship to the generation of sound waves by the ultrasound transceiver.

It is another object of the present invention to provide a needle design that allows visualization that does not impede the smooth passage of the needle through the surrounding tissue.

It is yet another object of the present invention to provide an improved needle design that allows visualization of the distal tip of the needle, thus allowing the physician to visualize the extreme distal end of the needle set.

It is yet another object of the present invention to provide a needle with engagement means for example, a change in profile proximal to needle tip to enhance safety feature thereof.

It is yet another object of the present invention to provide a needle with enhanced sound wave reflectivity for echogenicity.

It is another object of the present invention to provide a compact design for a needle having safety mechanism.

In accordance with one of the embodiments of the present invention, there is provided a safety introducer needle assembly having an introducer needle defining an axial direction. The needle having an outer surface and an inner surface defining a lumen which extends along the length of the needle in the axial direction. The outer surface is defined by a wall of the needle forming a needle shaft that extend along the axial direction having a distal end and a proximal end, wherein the proximal end is connected to a needle hub and the distal end comprises a sharp bevelled tip wherein the needle alternatively or additionally have a roughened or echogenic region that may include one or more projections, depressions, voids, grooves, ribs and/or protuberances of the types described further below. Proximal from the needle tip the needle shaft is provided with an engagement means for preventing a needle tip protector housed in a safety barrel and slidably arranged on the needle shaft from moving beyond the needle tip. The safety barrel is engageably attached to the needle hub.

Some embodiments of the present invention further comprise at least one safety barrel engaging element configured to restrict the rotation of the safety barrel and in turn of the needle tip protector with respect to the needle hub. The needle hub may comprise a corresponding safety barrel anti-rotation element configured to engage the safety barrel engaging element. The safety barrel can be snap fitted with the needle hub. The snap fit may be formed by the engaging element comprising a needle hub having a peripheral wall projecting from a distal surface. The peripheral wall of the needle hub can comprise at least one slit or recess, which passes through the thickness of the distal surface. The safety barrel can have at least one lateral protrusion from edge of the proximal surface configured to be received by the slit or recess within the needle hub forming a snap fit arrangement. The lateral protrusion can support the holding of the safety barrel with the needle hub. Thus, the safety barrel can be snap fitted with the needle hub. The snap-fit may be formed by a protrusion and a corresponding recess which can be provided in both needle hub and safety barrel alternatively. Other ways and means for a secure engagement are also encompassed.

Some embodiments of the present invention further comprise a curved profile of the safety barrel. The curved profile may simplify assembly of the safety barrel with the needle hub.

As well known in the art, the needle may also have a needle feature close to its needle tip, which interacts with a proportional base of the needle tip protector or needle guard, e.g. an enlargement, a curving or a bulge or crimp any other change in profile. Thereby, it can be prevented that the needle is retracted out of the needle tip protector, which is known in the art.

The invention also relates to a medical device for example, a safety introducer needle assembly including a needle tip protector housed in a safety barrel and further including a needle with echogenic feature having a needle shaft, a needle tip and a needle hub. The needle tip protector being housed in the safety barrel is slidably arranged on the needle, wherein the needle tip protector is movably retained in the inner space of the safety barrel when the needle extends there through, and wherein the needle tip protector captures the needle tip once it is received in the needle tip protector upon withdrawal of the needle in protected position. The inner space of the safety barrel defines a chamber ensuring that a first and second arms of the needle tip protector do not engage or interact with an inner surface of the chamber prior and during venipuncture of a patient. The needle tip protector of this kind is generally known. The needle tip protector serves to prevent a person handling the intravenous catheter apparatus from accidentally coming into contact with the needle tip post removal of the needle from a patient's vein. Thus, the safety introducer needle assembly helps to avoid unwanted transmission of blood borne diseases.

The improved needle tip design according to the present invention can be used on the needles of either manual or automated biopsy needle instruments used for the performance of tissue extraction or fluid aspiration visualized under ultrasound guidance.

BRIEF DESCRIPTION OF THE ACCOMPANYING DRAWINGS

The foregoing and other objects, features, and advantages of the invention will be apparent from the following detailed description taken in conjunction with the accompanying drawings, wherein.

DESCRIPTION OF THE INVENTION

Figure 1A:
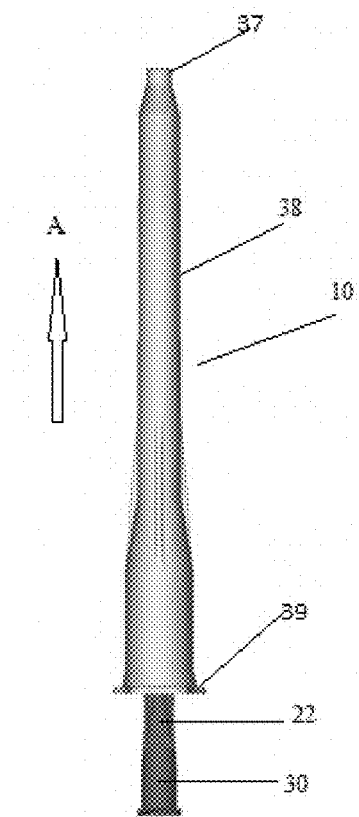
FIGS. 1A & 1B illustrate the overall view of a safety introducer needle assembly according to the present invention.

Embodiments of the presently disclosed invention will now be described in detail with reference to the drawings wherein like reference numerals designate identical or corresponding elements. In the drawings and in the description, the term "proximal", "bottom". "down" or "lower" refers to a location on the device that is closest to the medical practitioner using the device and farthest from the patient in connection with whom the device is used when the device is used in its normal operation. Conversely, the term "distal". "top". "up" or "upper" refers to a location on the device that is farthest from the clinician using the device and closest to the patient in connection with whom the device is used when the device is used in its normal operation. For example, the distal region of a needle will be the region of the needle containing the needle tip which is to be inserted e.g. into a patient's vein.

As used herein, the term "echogenic" describes the characteristic ability of a surface or device to direct a relatively favorable quality and quantity of an ultrasound signal back to a transducer for imaging purposes in comparison to a surface or device (or portion thereof) which is less echogenic, non-echogenic, or echolucent. In other words, a device or surface with increased echogenicity (or greater echogenic response) provides enhanced ultrasound imaging capabilities compared to a device or surface which is less echogenic or more echolucent. As used herein, "echogenic" and "echogenicity" typically refers to characteristics of device for example a needle having a sharp tip when device is positioned within a body conduit or other such environment where fluids and/or body tissues surround device.

As used herein, the term "in" or "inwardly" or "inner" refers to a location with respect to the device that, during normal use, is the inside of the device. Conversely, as used herein, the term "out" or "outwardly" or "outer" refers to a location with respect to the device that, during normal use, is toward the outside of the device.

The term "patient" should be understood to refer to a human or other animal and the term "medical personnel" should be understood to refer to a doctor, nurse, or clinician or medical practitioner or other care provider and may include support personnel.

As used herein, the terms first, second, third, etc. are understood to describe different structures/elements so as to distinguish one from another. However, the terms are not structurally limiting unless the context indicates otherwise.

The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Moreover, the Figures may show simplified or partial views, and the dimensions of elements in the Figures may be exaggerated or otherwise not in proportion for clarity. In addition, the singular forms "a," "an," and "the" include plural referents unless the context clearly dictates otherwise. Thus, for example, reference to a terminal includes reference to one or more terminals. In addition, where reference is made to a list of elements (e.g., elements a, b, c), such reference is intended to include any one of the listed elements by itself, any combination of less than all of the listed elements, and/or a combination of all of the listed elements.

As used herein "ready position" means the safety introducer needle assembly is ready for use, such as to perform a venipuncture or intravenous access. Sometimes the ready position first requires removing a protective cap from the catheter assembly or needle assembly. The protective cap can be included for packaging.

As used herein "protected position" means the safety introducer needle assembly in particular the needle hub having a needle is ready for disposal in that the needle tip is safely guarded by a needle tip protector.

Figure 1B:
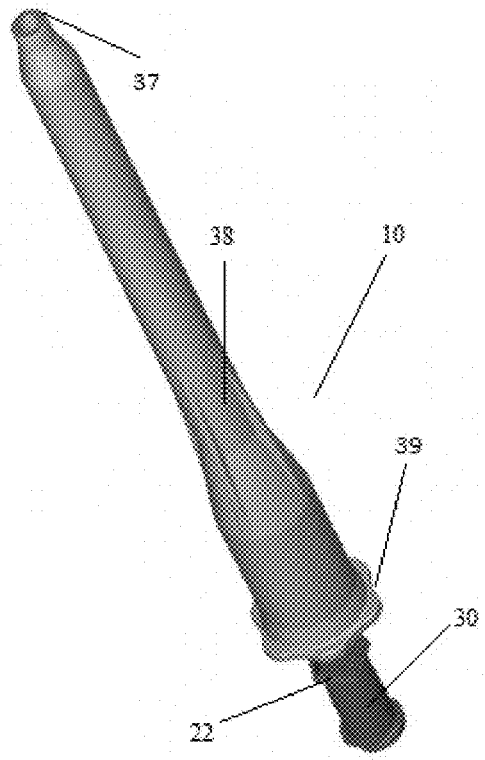

Referring now to FIGS. 1A & 1B an overall view of a safety introducer needle assembly 10 according to the present invention is shown comprising a protective needle cover 38 which is attached to a needle hub 22. The needle hub 22 can be provided with or without wings. The protective cover 38 can be formed of a plastic or metal or other suitable material and has inner space. In various embodiments, the outer periphery and/or inner periphery of the protective cover 38 body at its proximal end 18 can include one or more luer threads or the like in any number of thread configurations available to provide and interlock between the protective cover 38 and needle hub 22.

The inner space of the protective cover 38 receives the needle 12 and a safety barrel 42 housing a needle tip protector 40 which is movably arranged on the needle shaft 14. The inner space of the protective cover 38 may be parallel to the axial direction and defined between a distal end section 37 and a proximal end section 39 of the protective cover 38. The dimension of the inner space at the proximal end section is bigger in size in comparison to dimension of the inner space at the distal end section of the protective cover 38. The advantage of change in dimension of inner space lies in the fact that inner space at the proximal end section of the protective cover 38 is dimensioned very precisely in order to ensure an inner space with a well-controlled and large enough diameter such that no part of the safety barrel 42 when housed in the inner space of the protective cover 38 contact inner surface of the protective cover 38.

It should be understood that device 10 could be any of a variety of types of safety introducer needle assembly which are used for percutaneous, subcutaneous or other internal applications involving ultrasound imaging and therapeutic techniques (e.g. biopsy needles, intravascular devices, laparoscopic tools, etc.).

Figure 2A:
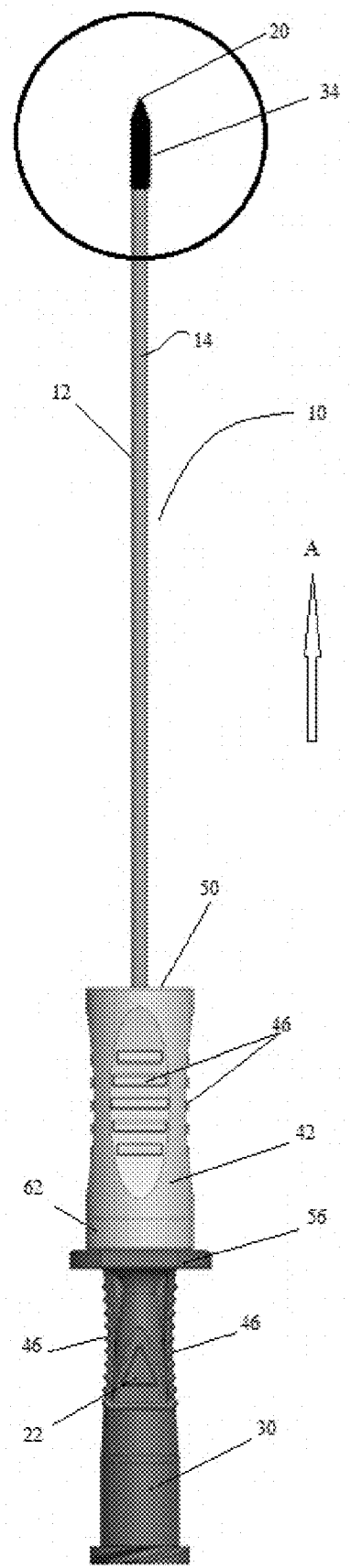
FIGS. 2A & 2B illustrate a safety introducer needle assembly without a needle cover according to the present invention.
Figure 2B:
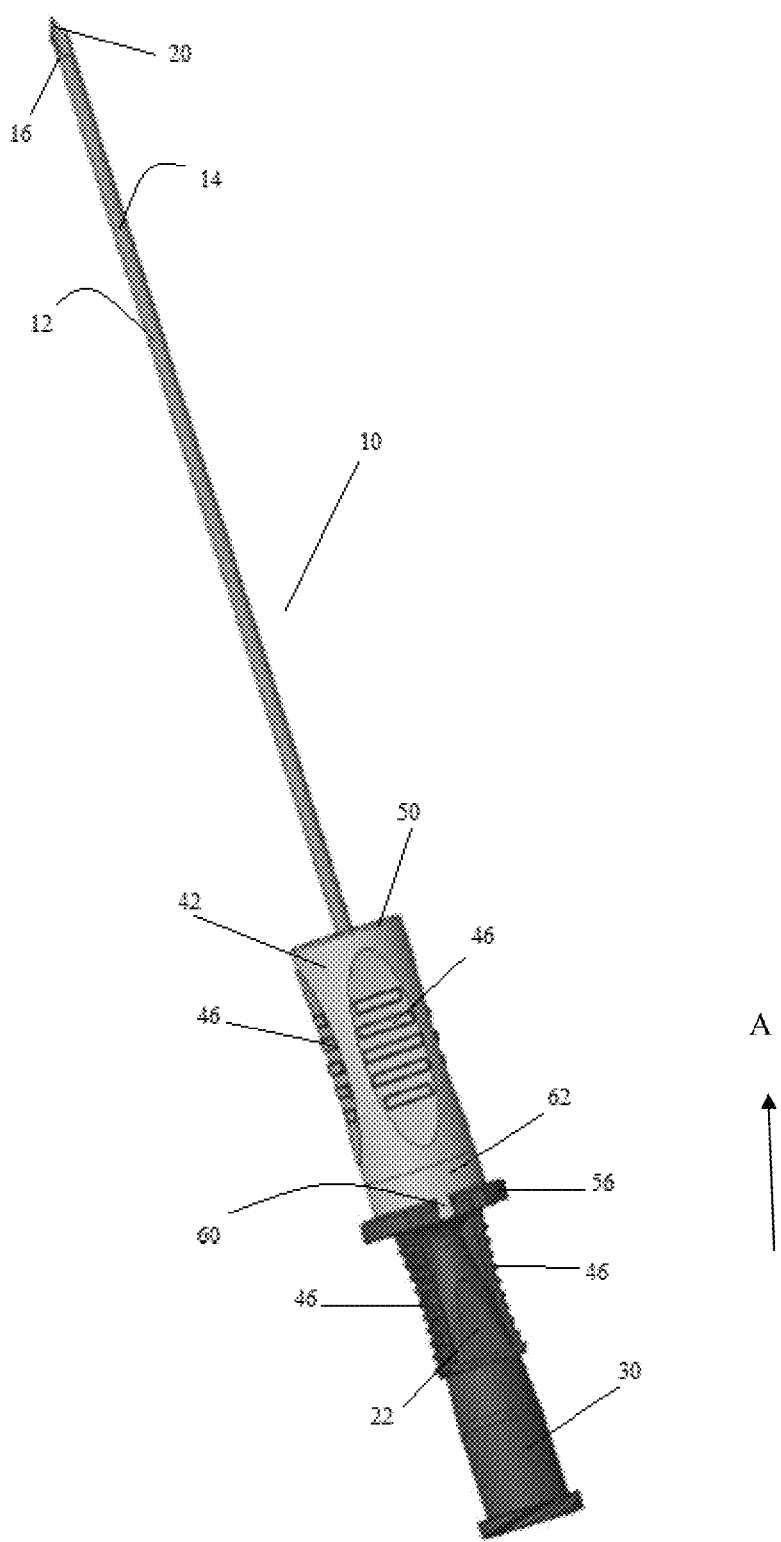
Figure 4A:
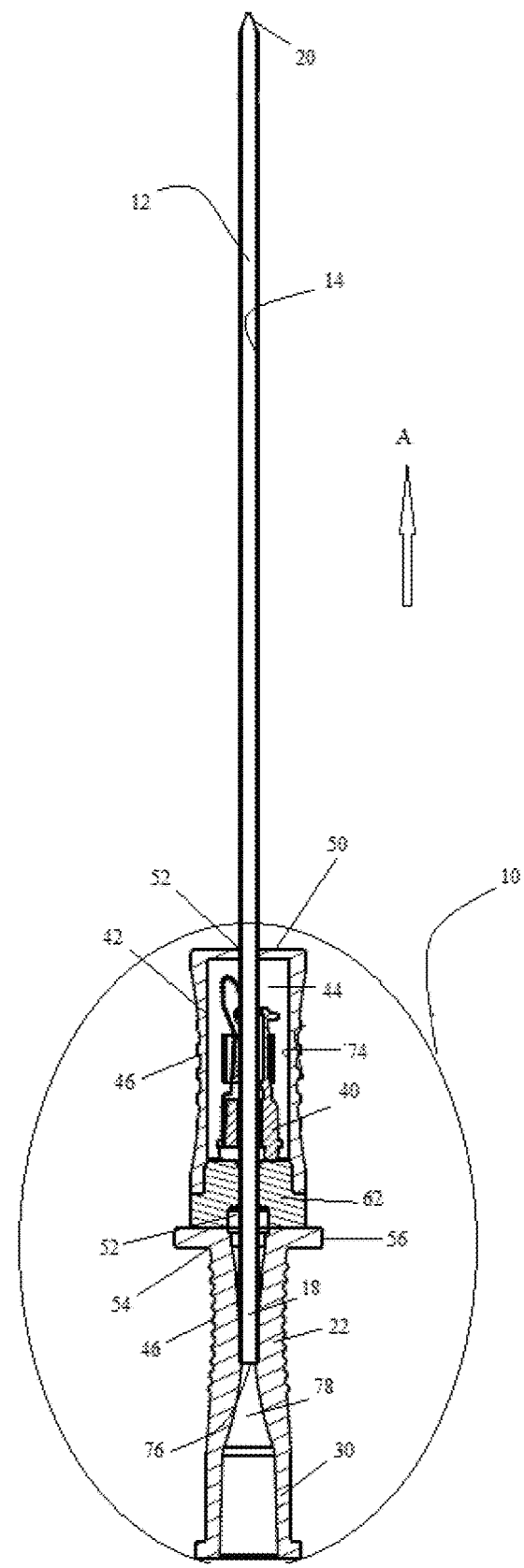
FIG. 4A illustrates a cross-sectional view of the safety introducer needle assembly shown in FIG. 2A showing a ready position according to the present invention.
Figure 4B:
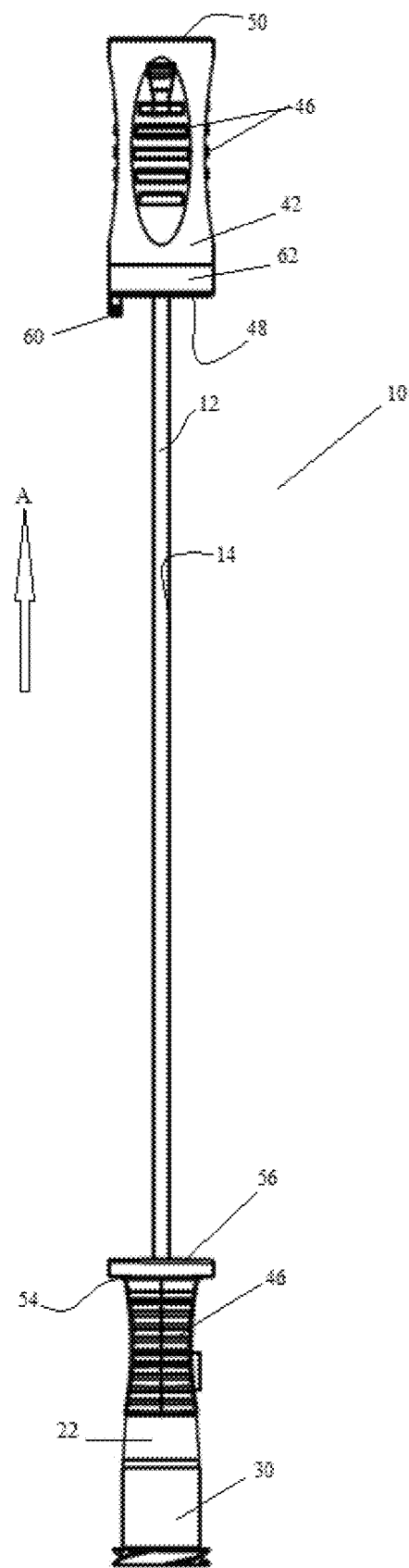
FIG. 4B illustrates a side view of the safety introducer needle assembly shown in FIG. 2A showing a protected position according to the present invention.
Figure 4C:
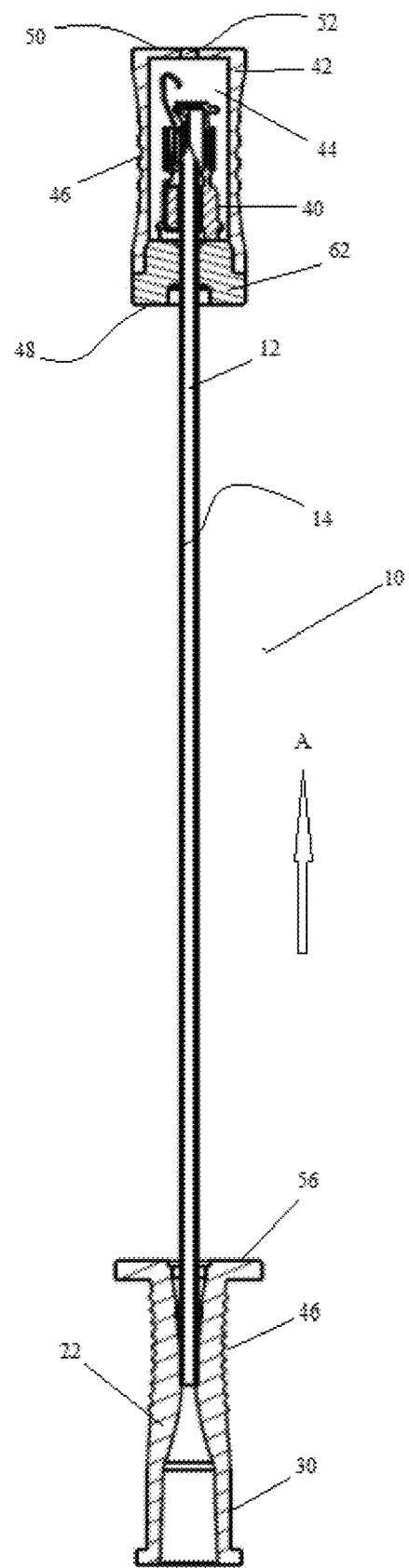
FIG. 4C illustrates a cross-sectional view of the safety introducer needle assembly shown in FIG. 2A showing a protected position according to the present invention.

FIGS. 2A and 2B illustrate a safety introducer needle assembly 10 without the needle cover 38 and show a needle 12 having echogenic feature defining an axial direction A. A needle tip protector 40 as shown in FIGS. 4A to 4C is movably arranged on the needle shaft 14 and retained in a safety barrel 42. The safety barrel 42 is engageably attached to the needle hub 22 prior to use of the device 10 in ready position as shown in FIGS. 2A & 4A.

Figure 2C:
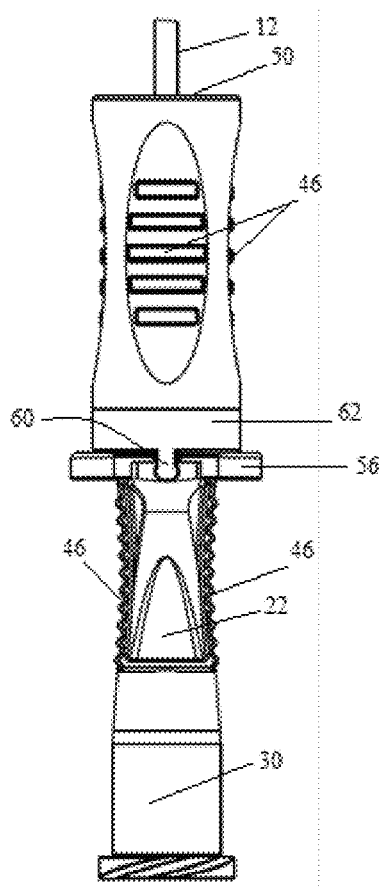
FIGS. 2C & 2D illustrate a partial enlarged views of safety introducer needle assembly showing the locking arrangement between the safety barrel and the needle hub according to the present invention.
Figure 2D:
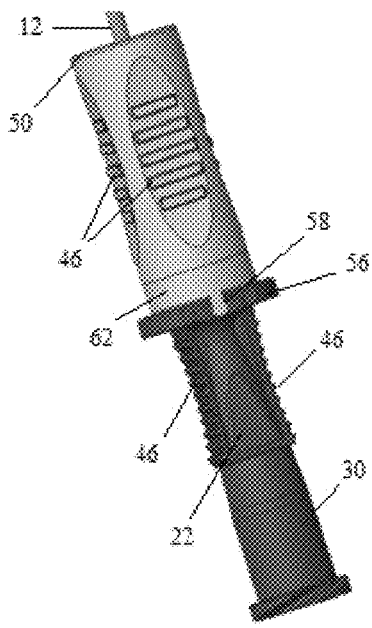

Referring now to FIGS. 2C & 2D which show enlarged views of the locking arrangement between the safety barrel 42 and the needle hub 22 comprising at least one safety barrel engaging element configured to restrict the rotation of the safety barrel 42 and in turn of the needle tip protector 40 with respect to the needle hub 22. The needle hub 22 is provided with a corresponding safety barrel anti-rotation element configured to engage the safety barrel engaging element. As shown in FIGS. 2C and 2D, the safety barrel 42 is snap fitted with the needle hub 22. The snap fit is formed by the engaging element comprising the needle hub 22 having a peripheral wall 56 projecting from a distal surface 54 of the needle hub 22. The peripheral wall 56 of the needle hub 22 comprises at least one slit or recess 58, which passes through the thickness of the distal surface 54. The safety barrel 42 is provided with at least one lateral protrusion 60 from edge of a proximal surface 48 configured to be received by the slit or recess 58 within the needle hub 22 forming a snap fit arrangement. The lateral protrusion 60 supports the holding of the safety barrel 42 with the needle hub 22. Thus, the safety barrel 42 is snap fitted with the needle hub 22. The snap-fit can also be formed by a protrusion and a corresponding recess which can be provided in both needle hub 22 and safety barrel 42 alternatively.

Alternative arrangements by way of replacing the change of dimensions outside the safety barrel 42 at the proximal end thereof and on the distal surface 54 or upper part of the needle hub 22 can also be employed. For example, the upper part of the needle hub 22 can be made with a fitment and be snap-fitted with the safety barrel 42. The snap-fit may be further formed by a protrusion ring and a corresponding groove ring. The protrusion ring may comprise the groove and the groove ring may comprise at least one projection or vice versa. The ring of both the projections or groove can be a continuous ring or a spaced apart formation. Other ways and means for a secure engagement are also encompassed.

Referring now to FIGS. 4A to 4C, the safety barrel 42 is provided with a proximal surface 48 formed by a barrel cap 62 and distal wall 50 wherein both the proximal surface 48 and distal wall 50 has a bore 52 to receive the needle 12. The inner diameter of the bore 52 has a close fit ratio with the outer diameter of the needle 12. The thickness of the proximal surface 48 is greater than the thickness of the distal wall 50. The safety barrel 42 is provided with inner space 44 defining a housing or chamber to movably receive the needle tip protector 40 as shown in FIGS. 4A and 4C. The needle tip protector 40 is received within the inner space 44 through a proximal end 18 of the needle 12 which is sealed with a barrel cap 62 forming the proximal surface 48. The barrel cap 62 is glued to the safety barrel 42 body using one or more adhesives in a fluid tight manner. The safety barrel 42 has a substantially cylindrical shape, which is structurally beneficial to the provision of rotation capabilities. The safety barrel 42 can have other geometrical shapes within the inner space 44 to house a needle tip proctor 40. The outer surface of the safety barrel 42 is provided with finger grips 46 for ease of handling, activation and easy movement and better grip. The safety barrel 42 is made of plastic material or glass having transparent qualities for visibility and designed with ergonomic feel for better control and ease of handling.

As can be seen in FIG. 4A, the proximal end 18 of needle 12 may comprise at least one opening 76 providing communication between a lumen of the needle 12 and a flash back chamber 78 provided in the needle hub 22 which is transparent to improve visibility and for instant flash back confirmation. The needle hub 22 is made of transparent plastic material to provide a view of the interior and thus of the blood therein. In the event of first venipuncture blood entering the lumen of the needle 12 can exit the needle 12 through the opening 76 and thus become visible for the person handling. The opening 76 is preferably large enough in order to provide a blood flashback function such that the practitioner can recognize that he has placed the needle 12 correctly within a patient's vein. In case of a correct positioning of the needle 12, blood pours out of the opening 76 within the flash back chamber 78 and visible through the transparent needle hub 22 and is visible to the practitioner. Alternatively, an opening 76 positioned close to the needle tip 20 can also be provided so that the blood does not have to travel the length of the needle 12 to enter the needle hub 22 in order to become visible. In such a case, blood entering the lumen of the needle 12 upon venipuncture partly exits the needle 12 near the needle tip 20 through the opening 76, thereby becoming particularly quickly and, thus, allowing for particularly fast venipuncture confirmation. The opening 76 may have a miniscule size which serves the purpose of early flashback detection and which does not obstruct the arms of the needle tip protector 40.

Figure 3:
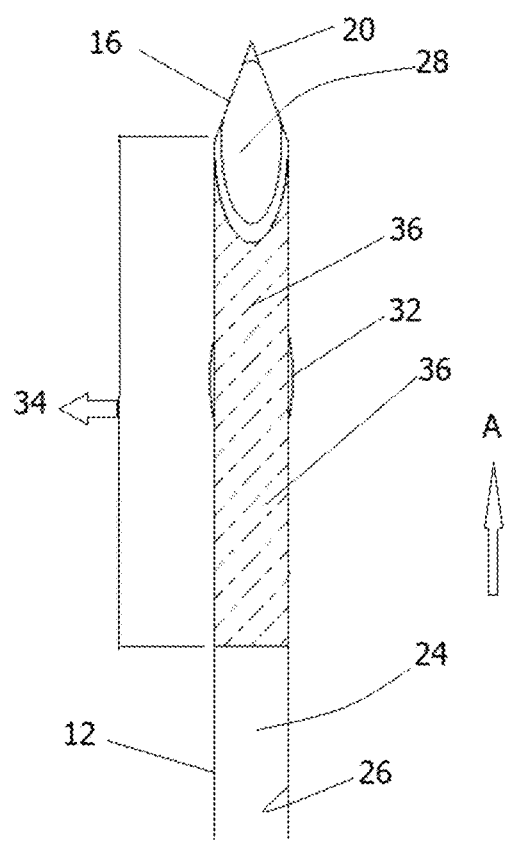
FIG. 3 illustrates an enlarged view of a distal portion of the needle encircled in FIG. 2A according to the present invention.

Referring now to FIG. 3, the needle 12 has an outer surface 24 and an inner surface 26 defining a lumen 28 which extends along the length of the needle 12 in the axial direction A. The outer surface 24 is defined by a wall of the needle 12 forming a needle shaft 14 that extend along the axial direction A having a distal end 16 and a proximal end 18, the distal end 16 comprises a sharp bevelled tip 20. Needle 12 may be made of a metal, a metal alloy, or any other material readily observable by ultrasound. In addition, needle 12 alternatively or additionally have a roughened or echogenic region 34 that may include one or more projections, depressions, voids, grooves, ribs and/or protuberances of the types described further below. Needle 12 can be used for providing a puncture site in blood vessels for the introduction of vascular access devices.

The proximal end 18 of the needle 12 is attached to a needle hub 22 which acts as a control end. The control end of device 10 may extend outside of the patient during use. Alternatively, the control end may attach to another piece that extends outside the patient. The control end generally ends in a handle 30 having one or more finger grips 46 or other operating portion for maneuvering device 10. Handle 30 can be any of a variety of forms or structures suitable for use in conjunction with needles or medical devices used in percutaneous applications.

Handle 30 is generally constructed to be manipulatable by hand in some embodiments and has a hollow axis in communication with lumen which can receive a stylet or other cylindrical objects or guide wires. In various embodiments, the outer periphery and/or inner periphery of the needle hub 22 body at its proximal end 18 can include one or more luer threads or the like in any number of thread configurations available to provide and interlock between mating devices. The luer threads allow another medical device having a male luer lock to be connected to and interlocked with the needle hub 22. In this manner, a separate access device can be coupled to the safety introducer needle assembly 10 through the needle hub 22 port to establish fluid communication there through. Alternatively, the needle hub 22 body can also have no luer threads to accommodate luer slip and luer lock connections.

Proximal from the needle tip 20 the needle shaft 14 is provided with an engagement means 32 for preventing a needle tip protector 40 which is housed in a safety barrel 42 and slidably arranged on the needle shaft 14 from moving beyond the needle tip 20. The engagement means 32 may comprise any form of irregularity of the needle shaft 14, for example, an enlargement of the outer profile of the needle shaft 14 at least in one direction transverse to the axial direction A.

In the illustrated embodiment, the engagement means 32 comprises a change in profile in the form of a crimped portion of the needle shaft 14. The enlargement is made by a crimping of the needle shaft 14. The change in profile 32 has an outer profile one dimension of which is larger than a maximum dimension of the profile of the through-bore of a stopping element provided in a needle tip protector 40. However, other ways of forming the enlargement are possible, such as applying additional material to the needle shaft 14, e.g. by soldering, welding or gluing etc. In alternative embodiments, the change in profile 32 can be provided anywhere between the distal end 16 and the proximal end 18 of the needle shaft 14.

The inner profile of the needle can either be reduced in the region of the enlargement 32, for example, if the enlargement 32 is formed by crimping, or it can be substantially constant throughout the length of the needle 12, for example, if the enlargement 32 is formed by applying additional material to the needle shaft.

Referring further to FIG. 3, it illustrates distal end 16 of the needle 12 encircled in FIG. 2A. The needle 12 has one or more echogenic regions (for example, echogenic region 34). The echogenic region 34 is provided with one or more echogenic features 36 that enhance the echogenicity of device 10. The echogenic region 34 is at least a portion of the needle 12, and in particular embodiments is at least a portion of outer surface 24 of the needle 12. Echogenic feature 36 may include projections, depressions, voids, grooves, ribs and/or protuberances or a combination thereof forming rough surface in the outer surface 24, which can have any of several possible geometric configurations.

In the embodiment shown in FIGS. 2A and 3 the combination of projection and grooves forming the echogenic feature 36 have a spiral form having helical grooves. The echogenic feature 36 also includes providing features in the form of a concave surface which has multiple angles and corners which are of assistance in reflecting ultrasound images. The helical groove can have a constant pitch or helical angle, multiple pitch angles (increasing or decreasing pitch angle) and/or include multiple grooves. In some embodiments, echogenic features 36 can be arranged to span longitudinally along outer surface 24 and along the longitudinal axis. In other embodiments, the depth of echogenic features 36 varies over the echogenic range/region 34. This variance can extend even to echogenic features 36 having the same helical groove or projection. Similarly, the relative angles between the walls (or surfaces) of echogenic features 36 can vary along the longitudinal axis.

In this unique configuration, the smaller radius captures the higher frequency of ultrasound and the larger radius captures the lowest or lower frequency of the ultrasound. Some prior art devices include ridges or bumps that extend above the needle or device surface which increase echogenicity but also increase drag force which is painful for the patient and can cause tenting or damage of the vessels or other internal body parts upon insertion or removal of the device from a patient. The echogenic feature 36 of the invention has a configuration which ensures that while retracting it does not increase the drag force and does not cause pain to the patient. Beneficially it has been found that these configurations increase echogenicity of the device 10 and improve image quality with ultrasound.

The echogenic features 36 can occupy a portion or all of tip 20, a region adjacent to tip 20, or other parts of device 10 or needle 12. In the embodiment of FIGS. 2A and 3, an echogenic region 34 is positioned near tip 20 so that not only can device 10 be located during ultrasound procedures but also tip 20 can be more accurately positioned during ultrasound procedures. In some other embodiments, one or more echogenic regions 34 can also be positioned further from tip 20, and can be spaced a known distance apart to provide information to a user during ultrasound procedures, such as the distance of insertion of a needle 12 or the proximity of the tip 20 to certain body tissues.

During use, device 10 having the echogenic feature 36 is inserted into a body conduit either through puncture or through an existing body conduit. An ultrasound imaging system including a console is used to image device 10 during insertion and while maneuvering device 10 to a desired location within the body. The ultrasound imaging system includes a transducer which is applied to the external surface of the body. The transducer transmits ultrasound signals generally towards device 10. Device 10 scatters and/or reflects a certain amount of the ultrasound signal back to the transducer. The transducer receives the returned ultrasound signal and transmits appropriate information to the console. The console displays an image which shows device 10 surrounded by body tissues and fluids. It is preferable for device 10 to appear with greater clarity and brightness than the surrounding body tissues and fluids. This is achieved by providing device 10 with enhanced echogenic properties. Echogenic feature 36 including a combination of projections and grooves provide device 10 with enhanced echogenic properties. Use of such echogenic features enhances echogenicity as compared to a smooth surface for a similar object. Device 10 having echogenic features 36 is capable of providing enhanced ultrasound visualization throughout a wide range of ultrasound frequencies and relative angles between device 10 and the transducer.

The construction and shape of the needle having echogenic feature 36 according to the various embodiments of the present disclosure provides a simple configuration. The simple and compact design of the needle for echogenicity according to the above disclosure is advantageous in a clinical setting because it provides an enhanced sound wave reflectivity for the safety and efficacy of ultrasound-guided medical devices and an automatic protection against accidental pricking by the needle tip thereby reducing injury or discomfort to a patient and provides better safety features. In addition, such design greatly reduces manufacturing costs and is efficient, effective and simple in its construction and use.

To explain further referring to FIGS. 4A to 4C, the use of echogenic needle with the needle tip protector 40 housed in a safety barrel 42, the safety introducer needle assembly 10 for example, the safety introducer needle assembly of the invention comprises a needle 12 defining an axial direction and having a needle shaft 14 and a needle tip 20 at a distal end 16 of the needle shaft 14. The needle shaft 14 comprises an engagement means 32 in the form of for example, a change in profile of the needle shaft 14 which is adapted to engage with a needle tip protector 40 slidably arranged on the needle shaft 14 in order to prevent the needle tip protector 40 from sliding off the needle tip 20.

The needle 12 having echogenic feature 36 post use is protected by a needle tip protector 40 housed in a safety barrel 42, wherein the needle tip protector 40 includes a base portion 70 made of a first material and having a needle passage which extends in an axial direction A from a proximal side of the base portion through the base portion 70 to a distal side of the base portion 70, such that a needle 12 having a principal outer profile can be movably arranged in the needle passage. The needle tip protector 40 further includes first 64 and second arms 66 extending substantially in the axial direction from the distal side of the base portion, with the first arm 64 having a distal region and a proximal region. A distal wall 68 is transversely arranged in the distal region of the first arm 64. The distal wall 68 is having a length and width much bigger than the outer diameter of the needle 12 such that it completely covers and blocks the needle tip 20 in protected position.

The needle tip protector 40 also includes a stopping element which is slidably arranged on the needle shaft and movable relative to the base portion. The stopping element is adapted to engage with an enlargement of the needle shaft 14 on its one side and with the base portion on its opposite side and, thus, effectively helps to prevent the needle tip protector from sliding beyond the needle tip 20, i.e. from being separated from the needle 12.

According to an embodiment, the stopping element completely surrounds the needle 12. The length of the stopping element, i.e. its dimension seen in the axial direction, may vary. As such, the stopping element can, for example, be a disk, a ring, or a tube. According to an alternative embodiment, it is also possible that the stopping element only partly surrounds the needle. In this case, the stopping element could have the shape of a slotted disk, ring, or tube. Furthermore, it has to be understood that outer profile of the stopping element does not have to have a circular outer profile. It is also possible that the outer profile of the stopping element is of non-circular form, for example, of oval or polygonal shape.

According to an embodiment, the stopping element is arranged in the base portion. For example, the stopping element can be arranged in a cavity or cut out provided in the base portion. Alternatively, the stopping element can be arranged anywhere between the first and second arms.

According to a further embodiment, the stopping element is made of a second material different from the first material. Preferably, the second material is of greater hardness and/or stiffness than the first material. For example, the first material could be a plastic material and the second material could consist of a metal, a ceramic or a rubber material, or any other type of material which is stiff and not as easily distorted as the first material.

Prior to the use of the device 10, the needle tip protector 40 is arranged in the safety barrel 42 which is snap fitted with the needle hub 22. In this situation, the needle 12 extends completely through the needle tip protector 40, thereby deflecting the first arm of the needle tip protector 40 outwards. i.e. at an angle to the axial direction A, such that the distal wall of the first arm is supported on the needle shaft 14. Following the insertion of the needle 12 into a patient and subsequently when the needle 12 is withdrawn from the patient and the needle shaft 14 moves through the needle tip protector 40 while the needle tip protector 40 is retained in the safety barrel 42. Once the needle tip passes the transverse distal wall 68 of the needle tip protector 40, i.e. such that the needle shaft 14 no longer supports the distal wall 68, a restoring force ensures that the first arm 64 of the needle tip protector 40 is moved back into alignment with the axial direction of the needle tip protector 40, so that the needle tip is blocked by the distal wall 68 of the needle tip protector 40, i.e. the needle tip 20 is prevented from axially projecting out of the safety barrel 42.

Figure 4D:
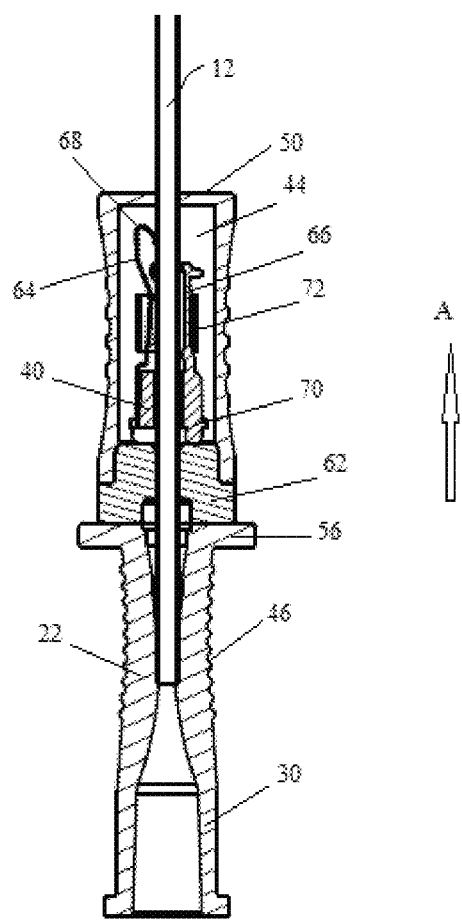
FIG. 4D illustrates a cross-sectional enlarged view of the safety barrel having a needle tip protector encircled in FIG. 4A in a ready position according to the present invention.

To explain further and referring now to FIG. 4D, the first arm 64 of the needle tip protector 40 which is housed in the safety barrel 42 can be longer than the second arm 66 and has a massive distal wall 68 having an undercut for catching the needle tip 20. The distal wall 68 is arranged at a distal end 16 of the first arm 64 and extends in a direction transverse to an axial direction A of the needle 12 such that the distal wall 68 completely blocks the needle 12. The distal wall 68 ensures that the needle tip 16 is prevented from axially projecting out or sideways projecting out of the needle tip protector 40. The distal wall 68 has a bigger dimension than the distal surface of the second arm 66 and much bigger dimension than the outer diameter of the needle 12 such that the distal wall 68 completely covers and blocks the needle tip 20 once confined and entrapped within the needle tip protector 40. The first and second arms 64, 66 of the needle tip protector 40 extend generally in the axial direction A from a distal side of the base portion 70, i.e. generally parallel to the needle shaft 14.

In the ready position, the first arm 64 deflects outward of the needle tip protector 40 such that the distal wall 68 of the first arm 64 is supported on the needle shaft 14. Further, in this ready position, the first and second arms 64, 66 do not engage or interact with an inner wall/surface of the safety barrel 42 prior and during venipuncture of a patient. This non-contact of the first and second arms 64, 66 with the inner surface of the safety barrel 42 significantly decreases the withdrawal force required and friction caused when a needle 12 is withdrawn through a patient being protected by a needle tip protector 40 after use. The safety barrel 42 of the invention is clear, colorless and transparent. To this end, the safety barrel 42 is made of optically clear material such as a plastic material or a rigid plastic material having transparent qualities such as glass or the like for visibility and designed with ergonomic feel for better control and ease of handling. The embodiments of the invention include a safety barrel 42, which may be made of optically clear material, rigid plastic material and/or other chemicals or in the alternate the safety barrel 42 can be made colored being non-transparent as well.

Once the needle tip is blocked by the distal wall 68, the enlargement 32 of the needle shaft 14 engages with the stopping element arranged in the base portion 70, to prevent the needle tip protector 40 from being removed from the needle shaft 14. The fact that the stopping element is made from a second material which is harder and less easily distorted than the first material of the base portion, has the effect that the needle tip protector 40 is secured more effectively on the needle shaft and can be retained in the safety barrel 42 even if excessive external force is applied when pulling on the needle, as the enlargement 32 is prevented from being pulled through the base portion 70 of the needle tip protector 40 due to the stopping element. Hence, it is less likely that the needle tip protector 40 is removed from the needle tip 20 accidentally and, as a result, the needle tip protector 40 being housed in the safety barrel 42 provides a better protection against accidental pricking and thus increased safety for the person handling the device 10.

In a further embodiment of the needle tip protector 40, a tension element 72 surrounds the first 64 and second 66 arms of the needle tip protector 40. In the deflected state of the first arm 64, the tension element 72 is expanded against a restoring force of the tension element 72. Once the needle shaft 14 no longer supports the distal wall 68, the tension element aids the repositioning of the first arm back into axial alignment with the axial direction. This repositioning is necessary so that the distal wall 68 can block the needle tip 20 from axially sliding out of the needle tip protector 40 and out of the safety barrel 42. In addition, the tension element helps to enclose a space between the first and second arms 64, 66. In other words, the tension element 72 adds to the protective effect of the needle tip protector 40.

The device 10 is particularly inexpensive to manufacture if the base portion 70, the first and second arms 64, 66 of the needle tip protector 40 are integrally made from a first material.

The first material may, for example, be a plastic material. Thus, the base portion 70, the first and second arms 64, 66 could be manufactured by injection molding.

Alternatively, the base portion 70, and one of the first and second arms 64, 66 can be integrally made from a first material. e.g. a plastic material, and the other one of the first and second arms 64, 66 can be made from a second material different from said first material. For example, said other one of the first and second arms 64, 66 can include a strip of material having spring-like properties. e.g. a strip of sheet metal, providing the above-mentioned inherent elasticity.

The restoring force is created by at least one of an elastic property of the first arm 64 and an additional tension element 72. The tension element 72, for example, a rubber band or the like, surrounds the first and second arms 64, 66. The tension element 72 at least partly surrounding the arms 64, 66 by a linear biasing action. Alternatively or additionally, the first 64 and second 66 arms can be made of a resilient material having elastic properties.

The construction and shape of the improved device 10 according to the various embodiments of the present disclosure provides a simple configuration. The simple and compact design of the device 10 according to the above disclosure is advantageous in a clinical setting because it smoothens the whole process thereby reducing injury or discomfort to a patient and provides better safety features. In addition, such design greatly reduces manufacturing costs and is efficient, effective and simple in its construction and use.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, from the foregoing description, it will be apparent to one of ordinary skill in the art that many changes and modifications can be made thereto without departing from the spirit or scope of the invention as set forth in the claims.

As can be appreciated, the echogenic needle described above is not limited to use in needle aspiration devices, but rather, may be used in other devices that use hollow needles, such as injection needle devices, or in any other device in which visibility to ultrasound may be desirable.

Accordingly, it is not intended that the scope of the foregoing description be limited to the exact description set forth above, but rather that such description be construed as encompassing such features that reside in the present invention, including all the features and embodiments that would be treated as equivalents thereof by those skilled in the relevant art.

The scope of the present invention herein disclosed is not limited by the particular disclosed embodiments described above but determined only by a fair reading of the complete specification to be filed on this application.

LIST OF REFERENCE NUMERALS

10 medical device or safety introducer needle assembly
12 needle
14 needle shaft
16 distal end
18 proximal end
20 sharp beveled tip
22 needle hub
24 outer surface
26 inner surface
28 lumen
30 handle
32 engagement means/enlargement/change in profile/crimp
34 echogenic region
36 echogenic feature
37 distal end section
38 protective cover
37 proximal end section
40 needle tip protector
42 safety barrel
44 inner space
46 finger grips
48 proximal wall/surface
50 distal wall/surface
52 bore
54 distal surface of needle hub
56 peripheral wall
58 slit or recess
60 lateral protrusion
62 barrel cap
64 first arm
66 second arm
68 distal wall
70 base portion
72 tension element
74 inner surface
76 Opening
78 flash back chamber
A axial direction

The invention claimed is:

1. A safety introducer needle assembly comprising:
a needle defining an axial direction, the needle has a wall having an outer surface and an inner surface, the inner surface of the wall defining a lumen which extends along the length of the needle in the axial direction;
wherein the outer surface of the wall of the needle forms a needle shaft that extends along the axial direction, wherein the wall has a distal end and a proximal end, wherein the proximal end is connected to a needle hub and the distal end comprises a tip;
a safety barrel engagebly attached to the needle hub and comprising a proximal surface, wherein the safety barrel comprises at least one lateral protrusion extending from an outer edge of the proximal surface configured to be received by the needle hub; and
a needle tip protector housed in the safety barrel and movably retained in an inner space of the safety barrel when the needle extends therethrough, wherein the needle tip protector captures the needle tip once the needle tip is received in the needle tip protector upon withdrawal of the needle in a protected position.

2. The safety introducer needle assembly as claimed in claim 1, further comprising an echogenic feature.

3. The safety introducer needle assembly as claimed in claim 2, wherein the echogenic feature comprises at least one selected from the group consisting of projections, depressions, voids, apertures, grooves, ribs, protuberances and any combination thereof forming a rough surface in the outer surface of the wall of the needle.

4. The safety introducer needle assembly as claimed in claim 2, wherein a portion or all of the tip, a region adjacent to the tip, or other parts of the needle or the safety introducer assembly comprises the echogenic feature.

5. The safety introducer needle assembly as claimed in claim 1, wherein the needle tip protector is slidably arranged on the needle shaft, and wherein proximal from the needle tip the needle shaft is provided with an irregularity for preventing the needle tip protector from moving beyond the needle tip.

6. The safety introducer needle assembly as claimed in claim 5, wherein the irregularity of the needle shaft comprises an enlargement of the outer profile of the needle shaft at least in one direction transverse to the axial direction.

7. The safety introducer needle assembly as claimed in claim 1, wherein needle is made of a metal, a metal alloy, or any other material readily observable by ultrasound.

8. The safety introducer needle assembly as claimed in claim 1, wherein the needle tip protector comprises first and second arms and wherein the inner space of the safety barrel defines a chamber having an inner surface, wherein the chamber is structured such that the first and second arms of the needle tip protector do not engage or interact with the inner surface of the chamber prior and during venipuncture of a patient.

9. The safety introducer needle assembly as claimed in claim 1, wherein the safety barrel comprises a distal wall and a barrel cap forming the proximal surface and wherein both the proximal wall surface and the distal wall have a bore to receive the needle.

10. The safety introducer needle assembly as claimed in claim 1, wherein the proximal surface of the safety barrel is engaged with the needle hub at an initial stage.

11. A medical device, comprising:
   a needle hub, the needle hub comprising a peripheral wall having at least one slit or recess; and
   a safety introducer needle assembly comprising:
      a needle defining an axial direction, the needle has a wall having an outer surface and an inner surface, the inner surface of the wall defining a lumen which extends along the length of the needle in the axial direction;
      wherein the outer surface of the wall of the needle forms a needle shaft that extends along the axial direction, wherein the wall has a distal end and a proximal end, wherein the proximal end is connected to the needle hub and the distal end comprises a tip; and
      a safety barrel engagebly attached to the needle hub and comprising a proximal surface;
      a needle tip protector housed in the safety barrel and movably retained in an inner space of the safety barrel when the needle extends therethrough, wherein the needle tip protector captures the needle tip once the needle tip is received in the needle tip protector upon withdrawal of the needle in a protected position; and
      wherein the safety barrel is provided with at least one lateral protrusion extending from outer edge of the proximal wall of the safety barrel configured to be received by the at least one slit or recess formed within the peripheral wall of the needle hub.

12. The medical device as claimed in claim 11, wherein the safety introducer needle assembly further comprises an echogenic feature.

13. The medical device as claimed in claim 12, wherein the echogenic feature comprises at least one selected from the group consisting of projections, depressions, voids, apertures, grooves, ribs, protuberances or any combination thereof forming a rough surface in the outer surface of the wall of the needle.

14. The medical device as claimed in claim 12, wherein a portion or all of the tip, a region adjacent to the tip, or other parts of the needle or safety introducer needle assembly comprises the echogenic feature.

15. The medical device as claimed in claim 11, wherein the needle tip protector is slidably arranged on the needle shaft, and wherein proximal from the needle tip the needle shaft is provided with an irregularity for preventing the needle tip protector from moving beyond the needle tip.

16. The medical device as claimed in claim 15, wherein the irregularity comprises an enlargement of the outer profile of the needle shaft at least in one direction transverse to the axial direction.

17. The medical device as claimed in claim 11, wherein the needle is made of a metal, a metal alloy, or any other material readily observable by ultrasound.

18. The medical device as claimed in claim 11, wherein the needle tip protector comprises first and second arms and wherein the inner space of the safety barrel defines a chamber having an inner surface, wherein the chamber is structured such that the first and second arms of the needle tip protector do not engage or interact with the inner surface of the chamber prior and during venipuncture of a patient.

19. The medical device as claimed in claim 11, wherein the safety barrel comprises a distal wall and a barrel cap forming the proximal surface and wherein both the proximal surface and the distal wall have a bore to receive the needle.

20. The medical device as claimed in claim 11, wherein the proximal surface of the safety barrel is engaged with the needle hub at an initial stage.

\* \* \* \* \*

UNITED STATES PATENT AND TRADEMARK OFFICE
CERTIFICATE OF CORRECTION

PATENT NO. : 12,383,301 B2
APPLICATION NO. : 17/432789
DATED : August 12, 2025
INVENTOR(S) : Rishi Baid et al.

Page 1 of 1

It is certified that error appears in the above-identified patent and that said Letters Patent is hereby corrected as shown below:

In the Claims

Column 15, Line 15, in Claim 9 please replace "the proximal wall surface" with --the proximal surface--

Signed and Sealed this
Thirtieth Day of September, 2025

John A. Squires
*Director of the United States Patent and Trademark Office*